United States Patent [19]

Stutz

[11] B 3,993,752

[45] Nov. 23, 1976

[54] WOOD PRESERVATIVE CONTAINING ALKALI METAL CYANIDES

[75] Inventor: Robert E. Stutz, Los Altos Hills, Calif.

[73] Assignee: Koppers Company, Inc., Pittsburgh, Pa.

[22] Filed: Aug. 7, 1969

[21] Appl. No.: 848,336

[44] Published under the second Trial Voluntary Protest Program on March 30, 1976 as document No. B 848,336.

Related U.S. Application Data

[63] Continuation-in-part of Ser. No. 631,595, April 18, 1967, abandoned.

[52] U.S. Cl. .................................. 424/129; 21/7; 424/127; 424/131; 424/132; 424/133; 424/141; 424/145; 424/146; 424/148; 424/288; 424/289; 424/290; 424/291; 424/293; 424/294; 424/297; 424/347
[51] Int. Cl.² ........................................ A01N 11/00
[58] Field of Search ............... 424/27, 29, 129, 291, 424/148, 347; 21/7

[56] References Cited
UNITED STATES PATENTS

| | | | |
|---|---|---|---|
| 3,105,773 | 10/1963 | Frank et al. | 428/290 |
| 3,305,298 | 2/1967 | Chapman et al. | 424/148 |
| 3,305,442 | 2/1967 | Nishimoto et al. | 424/288 |

FOREIGN PATENTS OR APPLICATIONS

| | | | |
|---|---|---|---|
| 519,766 | 12/1955 | Canada | 167/38.5 |

OTHER PUBLICATIONS

Dessy, G., Chem. Abstracts, vol. 18 (1924), p. 3403.

Primary Examiner—V. D. Turner
Attorney, Agent, or Firm—Herbert J. Zeh, Jr.; Oscar B. Brumback

[57] ABSTRACT

An alkali metal cyanide added to alkaline borate buffered liquid fungicide concentrates of chlorophenates and organic or inorganic salts of mercury, lead, tin, copper and zinc provides a non-linial enhancement of fungistatic performance when used in the treatment of lumber and veneer and improved stability of the concentrates.

8 Claims, No Drawings

WOOD PRESERVATIVE CONTAINING ALKALI METAL CYANIDES

This application is a continuation-in-part of copending application Ser. No. 631,595, filed Apr. 18, 1967, and now abandoned.

This invention relates to a novel wood preservative composition which provides superior performance for fungal, mold and enzymatic stain control for lumber and veneer.

More particularly, this invention relates to an improved stain preventing wood preservative containing an alkali metal cyanide, metal salts, halogenated phenols and a buffer.

Several liquid fungicidal concentrates have been described for use on green lumber in the prior art. None of the chemical formulations so described appear to have been fully effective against the wide range of microorganisms involved. Some fungicidal-bactericidal systems controlled Ascomycetes and *Fungi-imperfecti* well, but were weak against certain molds, and other systems gave just the reverse pattern of results. Certain of the chemical solutions used to effect microbial control are unstable when recycled over the acidic wood and this results in formation of precipitates and sludges. The net effect of this behavior is to cause loss of strength and poor performance in the control of the microbial organisms.

The sodium 2,4,5-trichlorophenate, phenyl mercuric lactate, methanol system described in Canadian Pat. No. 715,048 is not particularly applicable to use in recycling spray or dip tank operations because of the absence of a buffer to maintain adequate alkalinity in the working solution. An improvement and advantage of using tetrachlorophenol with this system is taught in U.S. Pat. No. 3,305,298. The concentrate taught by this patent is comprised of technical tetrachlorophenol, sodium hydroxide, sodium tetraborate decahydrate, phenyl mercurial lactate, solvents and water. Sodium metaborate, derived from borax (sodium tetraborate decahydrate) and sodium hydroxide at pH 13 and carrying about one mole of excess sodium hydroxide, reduces buffering problems with the concentrate and working solutions in spraying and dipping applications.

In spite of these improvements, certain molds such as *Encephloascus fragrans sp.* (generally known as Ascocybe) and *Stemphyllium sp.* tend to flourish under moderately severe exposure conditions. These conditions also promote the development of internal stain in solid packaged, green, dimension lumber during storage.

It is therefore an object of this invention to provide compositions which provide superior performance for fungal, mold and enzymatic stain control for lumber during the seasoning process and most particularly to restrict the development of internal stain in packaged, dimension lumber with no increase in the cost of the treatment over existing systems.

It is a further object of the invention to provide improved stability of shelf life for the liquid concentrate during storage and the ready-to-use solutions prepared from those concentrates so that precise and reproducible dilution with water may be obtained with commercially available metering equipment.

Further objects, advantages and features of this invention will be apparent to those skilled in the art from the following description and claims.

In accordance with this invention unanticipated results are achieved by the action of desirable concentrations of soluble alkali metal cyanide, chlorophenates, sodium metaborate, metal salts and selected solvents in both liquid concentrates and dilute working solutions. Development of all stain and mold is inhibited to a remarkable degree when the compositions comprising proper ratios of these compounds are applied to apparently clean, stain-free, freshly sawn wood by dipping, spraying or otherwise. The use of the compositions of this invention has resulted in green lumber being more nearly maintained in a fresh cut condition than has heretofore been possible during storage, shipping or seasoning.

This invention provides a stable liquid sapstain concentrate comprising (1) from about 0.001% to about 40% by weight of an alkali metal cyanide; (2) from about 20% to about 90% by weight of water; (3) from about 0.05% to about 18% by weight of an alkali metal hydroxide; (4) from about 1% to about 22% by weight of an alkali metal borate; (5) from about 3% to about 15% by weight of an alkanol having from 1 to 4 carbons; (6) from about 3% to about 20% by weight of an organic solvent selected from the group consisting of acetone, methylethyl ketone, ethylene glycol, propylene glycol, glycerol, di-propylene glycol, tri-propylene glycol, ethylene glycol methyl ether, diethylene glycol ether, propylene glycol methyl ether and di-propylene glycol methyl ether; (7) from about 5% to about 40% by weight of halogenated phenols; and (8) from about 0.005% to about 5% by weight of a heavy metal salt.

Although sodium cyanide is preferred for use in the practice of this invention, lithium cyanide and potassium cyanide may also be used.

The alkali metal hydroxide used may be sodium lithium or potassium with the sodium hydroxide being preferred.

To effect buffering in the compositions of the instant invention, the borate ion used comprises soluble borates such as sodium borate, lithium borate and potassium borate, borax, borax decahydrate, sodium metaborate and other boron salts capable of conversion to sodium metaborate in solution. Sodium metaborate is used as the preferred buffer because it has the highest level of low temperature solubility in metastable systems. It is readily prepared from borax by direct causticization in solution.

A variety of solvents can be employed in the practice of the present invention. Such solvents consist of alkanols having 1 to 4 carbon atoms, acetone, methylethyl ketone, ethylene glycol, propylene glycol, glycerol, di-propylene glycol, tri-propylene glycol, propylene glycol methyl ether, di-propylene glycol methyl ether and others apparent to those skilled in the art.

The halogenated phenols that are useful in the invention include pentachlorophenol, 2,3,4,6-tetrachlorophenol, 2,3,5,6-tetrachlorophenol, 2,4,5-trichlorophenol, 2,4,6-trichlorophenol, and mixtures thereof. The use of a commercial mixture of chlorinated phenols that consists essentially of 2,3,4,6-tetrachlorophenol and pentachlorophenol is a preferred embodiment of this invention. Such a mixture contains from about 80% by weight of 2,3,4,6-tetrachlorophenol and about 20% by weight of pentachlorophenol. The replacement of such halogenated phenol systems with pentachlorophenol, sodium pentachlorophenate, or reasonable combinations of tetrachlorophenol, pentachlorophenol, the symmetrical and unsymmetrical trichlorophenols or their sodium salts is possible in compositions of the instant invention with changes in co-solvents and water to obtain maximum solubility and performance. Various levels of sodium cyanide and sodium metaborate may be used.

A wide variety of heavy metal organic and inorganic salts have been found to be useful in the practice of this invention. Such heavy metals include mercury, lead, tin, copper, zinc, cadmium, silver, arsenic and antimony. Examples of the mercury salts which can be used are phenyl mercuric lactate, phenyl mercuric acetate, phenyl mercuric hydroxide, phenyl mercuric propionate, phenyl mercuric borate, phenyl mercuric urea, phenyl mercuric chloride, phenyl mercuric nitrate, methyl mercuric acetate, ethyl mercuric acetate, methoxyethyl mercuric acetate, mercuric chloride, mercuric acetate, phenyl mercuric cyanide, methyl mercuric cyanide and 2,3,4,6-tetrachlorophenoxy mercuric cyanide. Organic tin salts which can be used include tributyl tin acetate, triphenyl tin acetate, tributyl tin chloride and triphenyl tin chloride and organic lead salts include tributyl lead acetate and triphenyl lead acetate. Soluble inorganic salts of lead, copper, tin and zinc are also applicable in the practice of this invention. Other inorganic metal salts which are employed include silver nitrate, arsenic chloride, cadmium chloride and antimony chloride.

Metal oxides such as mercuric oxide and tributyl tin oxide in addition to oxides of lead, copper, tin, zinc, silver, arsenic, cadmium and antimony are found to be useful in this invention. When lead, copper, tin, zinc or mercuric cyanide is converted into the corresponding halogenated phenoxy metallic cyanide, performance is found to be better than the mercury free test formulation.

Phenyl mercuric acetate and phenyl mercuric lactate are preferred embodiments in the practice of this invention.

Stable concentrates may be prepared with commercially available water miscible solvents selected from alcohols, ketones, polyols and others which include: methanol, ethanol, n-propanol, isopropanol, n-butanol, sec-butanol, acetone, methyl ethyl ketone, ethylene glycol, propylene glycol, glycerol, di-propylene glycol, tri-propylene glycol, propylene glycol methyl ether, di-propylene glycol methyl ether and others apparent to those skilled in the art.

Changes in the co-solvent portion of the formulation are necessitated when different chlorophenols are used and the concentrations of chlorophenol, sodium metaborate and cyanide are varied.

The cyanide containing sapstain concentrates can be prepared in the following manner in a suitable reactor: the alkali metal cyanide, water, sodium hydroxide and soluble borate are mixed and agitated to effect solution of the ingredients. While the mixture is under agitation, the solvent or solvents, chlorophenol and organic mercurial are added. The reaction mixture is heated to about 150°F and agitated to affect complete solution. Some preparations are turbid because of suspended insolubles in the chlorophenol or chlorophenate used. To speed the rate of solution of some phenyl mercurials, the desired amount may be dissolved or dispersed in the solvent and added after part of the chlorophenol or chlorophenate has dissolved. The sapstain concentrate can be used directly or may be filtered to remove minor amounts of insolubles which may be present.

The invention will be more fully understood by reference to the following examples. The examples, however, are given for the purpose of illustration only and are not to be construed as limiting the scope of the invention in any way.

In order to demonstrate the sapstain control effectiveness of the compositions of the instant invention, a number of compositions shown in Table I were prepared in accordance with the heretofore described procedures.

The compositions shown in Table I are used in that one volume of composition is diluted with 100 volumes of water. All of the examples are shown on a single volume basis except Example 18 which shows a two volume composition diluted with 100 volumes of water.

Ponderosa pine test pieces of 1 foot length, ½ inch thick and 1 inch wide are placed in test bundles containing 24 pieces stacked four wide and six high. The bundle is dipped and turned over in the test solution over a period of about 30 seconds.

TABLE 1

| Ingredients | Compositions Percent by Weight | | | | | | | |
|---|---|---|---|---|---|---|---|---|
| | 1 | 2 | 3 | 4 | 5 | 6 | 7 | 8 |
| Sodium cyanide | — | 0.1 | 0.3 | 0.5 | 1.0 | 2.1 | 4.2 | 7.1 |
| Water | 45.2 | 45.1 | 44.9 | 44.7 | 44.2 | 43.1 | 34.5 | 37.7 |
| Sodium hydroxide 50% | 6.8 | 6.8 | 6.8 | 6.8 | 6.8 | 6.8 | 13.1 | 11.2 |
| Borax | 9.5 | 9.5 | 9.5 | 9.5 | 9.5 | 9.5 | 9.2 | 7.8 |
| Propylene glycol methyl ether | 1.6 | 1.6 | 1.6 | 1.6 | 1.6 | 1.6 | 1.5 | 2.6 |
| Isopropanol | 4.7 | 4.7 | 4.7 | 4.7 | 4.7 | 4.7 | 6.5 | 5.6 |
| Ethylene glycol | 9.5 | 9.5 | 9.5 | 9.5 | 9.5 | 9.5 | 9.1 | 9.4 |
| Tetrachlorophenol[1] | 22.3 | 22.3 | 22.3 | 22.3 | 22.3 | 22.3 | 21.5 | 18.3 |
| Phenyl mercuric acetate | 0.4 | 0.4 | 0.4 | 0.4 | 0.4 | 0.4 | 0.4 | 0.3 |
| Gm. Conc./Gal. Ready to Use Solution | 47.5 | 47.7 | 47.7 | 47.8 | 47.9 | 48.2 | 49.0 | 58.2 |

[1]80% Tetrachlorophenol 20% Pentachlorophenol

| Ingredients | Compositions Percent by Weight | | | | | | | | | |
|---|---|---|---|---|---|---|---|---|---|---|
| | 9 | 10 | 11 | 12 | 13 | 14 | 15 | 16 | 17 | 18 |
| Sodium cyanide | — | 0.2 | — | 0.2 | 0.5 | 2.2 | 4.3 | 7.6 | — | — |
| Water | 44.2 | 46.0 | 38.3 | 38.1 | 37.8 | 36.1 | 34.0 | 36.8 | 42.0 | 42.0 |
| Sodium hydroxide 50% | 10.3 | 9.9 | 13.7 | 13.7 | 13.7 | 13.7 | 13.7 | 8.4 | 13.3 | 13.3 |
| Borax | 10.4 | 9.9 | 9.6 | 9.6 | 9.6 | 9.6 | 9.6 | 8.4 | 9.2 | 9.2 |
| Isopropanol | 5.2 | 5.0 | 4.8 | 4.8 | 4.8 | 4.8 | 4.8 | 6.1 | — | — |
| Dipropylene glycol | | | | | | | | | | |

TABLE 1-continued

| Ingredients | Compositions Percent by Weight | | | | | | | | |
|---|---|---|---|---|---|---|---|---|---|
| | 1 | 2 | 3 | 4 | 5 | 6 | 7 | 8 | |
| methyl ether | 0.9 | 1.6 | — | — | — | — | — | — | — |
| Ethylene glycol | 10.4 | 9.8 | 9.6 | 9.6 | 9.6 | 9.6 | 9.6 | 10.2 | 1.6 | 1.6 |
| Pentachlorophenol | 18.2 | 17.2 | — | — | — | — | — | — | — |
| Phenyl mercuric acetate | 0.4 | 0.4 | — | — | — | — | — | — | — |
| Tetrachlorophenol | — | — | 22.4 | 22.4 | 22.4 | 22.4 | 22.4 | 19.7 | — | — |
| Methanol | — | — | — | — | — | — | — | — | 9.7 | 9.7 |
| Propylene glycol monomethyl ether | — | — | 1.6 | 1.6 | 1.6 | 1.6 | 1.6 | 2.8 | 1.6 | 1.6 |
| Chlorinated phenols[1] | — | — | — | — | — | — | — | — | 22.2 | 22.2 |
| Phenyl mercuric lactate | — | — | — | — | — | — | — | — | 0.40 | 0.40 |
| Gm. Conc./Gal Ready to Use Solution | 43.5 | 46.3 | 47.1 | 47.4 | 47.5 | 47.8 | 48.9 | 56.0 | 46.5 | 93.0 |

[1] 70-82.5% 2,3,4,6-tetrachlorophenol 30-17.5% pentachlorophenol

TABLE II

| Example No. | Gal Composition per 100 Gal H$_2$O | % NaCN in Working Sol. | Blue Stain plus Internal Stain | | Total Stain and Mold | |
|---|---|---|---|---|---|---|
| | | | 6 wks | 12 wks | 6 wks | 12 wks |
| 1 | 1 | 0.0000 | 13 | 301 | 17 | 313 |
| 2 | 1 | 0.0017 | 2 | 151 | 4 | 156 |
| 3 | 1 | 0.0034 | 26 | 596 | 39 | 596 |
| 4 | 1 | 0.0068 | 64 | 747 | 86 | 747 |
| 5 | 1 | 0.0136 | 1 | 33 | 1 | 33 |
| 6 | 1 | 0.0292 | 1 | 24 | 1 | 24 |
| 7 | 1 | 0.0543 | 0 | 16 | 0 | 16 |
| 8 | 1 | 0.109 | 0 | 14 | 0 | 14 |
| 9 | 1 | 0.0000 | 34 | — | 209 | — |
| 10 | 1 | 0.0021 | 0 | — | 36 | — |
| 11 | 1 | 0.0000 | 483 | 743 | 538 | 848 |
| 12 | 1 | 0.0017 | 583 | 779 | 644 | 859 |
| 13 | 1 | 0.0068 | 643 | 1172 | 705 | 1197 |
| 14 | 1 | 0.0272 | 312 | 618 | 322 | 693 |
| 15 | 1 | 0.0543 | 644 | 998 | 676 | 1023 |
| 16 | 1 | 0.109 | 373 | 670 | 377 | 673 |
| 17 | 1 | 0.0000 | 23 | 122 | 30 | 122 |
| 18 | 2 | 0.0000 | 5 | 27 | 5 | 27 |
| Untreated Control | | | 2300 | 2387 | 4120 | — |

Examples 17 and 18 are commercial "A" product.

For comparative purposes, in addition to the untreated lumber, single and double strength applications of commercial preparations (Examples 17 and 18) are applied to Ponderosa pine bundles.

After a period of 6 weeks to 6 months exposure to summer, fall and winter conditions, the treated and untreated lumber is examined and the results obtained for stain and mold control are given in Table II. The individual pieces of wood in each package are scored as to the percentage of surface covered by the various degrading classes of micro-organisms. Blue stain is the sum of the percent of surface of the individual pieces covered by the fruiting bodies of this fungi. Internal stain is indicated by the discoloration which is the evidence of the blue stain organism growing beneath the treated surface. A maximum of 2400 is obtainable for untreated lumber which represents the total of the two values obtained.

Similar values are obtained for the decay fungus and various molds as the brown mold *Encepheloascus fragrans sp.* often called ascocybe, green molds which are often from the trichoderma group, and white molds which may be the forerunners of decay. The total mold and stain values shown in Table II are comprised of the sum of the values found in each package.

Although the instant invention is generally effective for fungicidal mold and enzymatic stain control for unseasoned lumber, it is understood that it may also be used for fibrous cellulosic materials such as pulp or paper and such agrinomic and other applications that may be apparent to those skilled in the art.

In addition to the treatment of Ponderosa pine, other woods such as Southern yellow pine and hemlock treated by the process and compositions of this invention exhibit excellent sapstain control.

In a manner similar to the examples in Table I, striking improvement in sapstain control is obtained when the sodium cyanide is replaced with lithium or potassium cyanide. Similar results are obtained when the mercurial used is phenyl mercuric lactate.

The concentrates prepared in the instant invention may be readily diluted 1:10 to 1:1000 in water to obtain compositions which are useful in the sapstain control art.

From the foregoing results it is evident that the compositions of this invention impart significant improvement in sapstain control over that resulting from the use of compositions of the prior art. Such improvements range from four to 30 times more efficient than obtained by the prior art when the same level of concentrations are used. It should be noted that twice the volume concentration of the prior art compositions (see Example 18) are required to approach the results obtained with the one volume concentration used in the practice of this invention.

While this invention has been described with respect to certain embodiments, it is not so limited and it is to be understood that variations and modifications thereof may be made without departing from the spirit or scope of this invention.

The embodiments of the invention in which an exclusive property or privilege is claimed are defined as follows:

1. A wood preservative composition comprising (1) from about 0.001% to 40% by weight of an alkali metal cyanide selected from the group consisting of lithium cyanide, sodium cyanide and potassium cyanide; (2) from about 20% to about 90% by weight of water; (3) from about 0.05% to about 18% by weight of an alkali metal hydroxide selected from the group consisting of lithium hydroxide, sodium hydroxide and potassium hydroxide; (4) from about 1% to about 22% by weight of an alkali metal borate selected from the group consisting of lithium borate, sodium borate and potassium borate; (5) from about 3% to about 15% by weight of an alkanol having from 1 to 4 carbons; (6) from about 3% to about 20% by weight of an organic solvent selected from the group consisting of acetone, methylethyl ketone, ethylene glycol, propylene glycol, glycerol, di-propylene glycol, tri-propylene glycol, ethylene glycol methyl ether, di-ethylene glycol methyl ether, propylene glycol methyl ether and di-propylene glycol methyl ether; (7) from about 5% to about 40% by weight of a halogenated phenol and (8) from about 0.005% to about 5% by weight of a heavy metal salt or oxide selected from the group consisting of inorganic and organic salts of mercury, lead, tin, copper, zinc, cadmium, arsenic, antimony and silver, and oxides of mercury, lead, tin, copper, zinc, cadmium, arsenic, antimony and silver.

2. A wood preservative composition comprising (1) from about 0.001% to 40% by weight of an alkali metal cyanide selected from the group consisting of lithium cyanide, sodium cyanide and potassium cyanide; (2) from about 20% to about 90% by weight of water; (3) from about 0.05% to about 18% by weight of an alkali metal hydroxide selected from the group consisting of lithium hydroxide, sodium hydroxide and potassium hydroxide; (4) from about 1% to about 22% by weight of an alkali metal borate selected from the group consisting of lithium borate, sodium borate and potassium borate; (5) from about 3% to about 15% by weight of an alkanol having from 3 to 4 carbons; (6) from about 3% to about 20% by weight of an organic solvent selected from the group consisting of acetone, methylethyl ketone, ethylene glycol, ethylene glycol methyl ether, di-ethylene glycol methyl ether, propylene glycol, glycerol, di-propylene glycol, tri-propylene glycol, propylene glycol methyl ether and di-propylene glycol methyl ether; (7) from about 5% to about 40% by weight of a halogenated phenol and (8) from about 0.005% to about 5% by weight of a mercury compound selected from the group consisting of inorganic salts of mercury, organic salts of mercury and mercuric oxide.

3. A composition as defined in claim 2 wherein the alkali metal cyanide is sodium cyanide.

4. A composition as defined in claim 2 wherein the alkanol is isopropanol.

5. A composition as defined in claim 2 wherein the alkali metal borate is sodium borate.

6. A composition as defined in claim 2 wherein the mercury compound is phenyl mercuric acetate.

7. A composition as defined in claim 2 wherein the mercury compound is phenyl mercuric lactate.

8. A wood product comprising wood contacted with a ready-to-use solution of a stable liquid sapstain concentrate comprising (1) from about 0.001% to 40% by weight of an alkali metal cyanide selected from the group consisting of lithium cyanide, sodium cyanide and potassium cyanide; (2) from about 20% to about 90% by weight of water; (3) from about 0.05% to about 18% by weight of an alkali metal hydroxide selected from the group consisting of lithium hydroxide, sodium hydroxide and potassium hydroxide; (4) from about 1% to about 22% by weight of an alkali metal borate selected from the group consisting of lithium borate, sodium borate and potassium borate; (5) from about 3% to about 15% by weight of an alkanol having from 1 to 4 carbons; (6) from about 3% to about 20% by weight of an organic solvent selected from the group consisting of acetone, methylethyl ketone, ethylene glycol, ethylene glycol methyl ether, di-ethylene glycol methyl ether, propylene glycol, glycerol, di-propylene glycol, tri-propylene glycol, propylene glycol methyl ether and di-propylene glycol methyl ether; (7) from about 5% to about 40% by weight of a halogenated phenol and (8) from about 0.005% to about 5% by weight of a heavy metal salt or oxide selected from the group consisting of inorganic and organic salts of mercury, lead, tin, copper, zinc, cadmium, arsenic, antimony and silver, and oxides of mercury, lead, tin, copper, zinc, cadmium, arsenic, antimony and silver.

* * * * *